United States Patent [19]

Rehmert, Jr.

[11] Patent Number: 4,910,209

[45] Date of Patent: Mar. 20, 1990

[54] METHOD OF TREATING PARASITIC INFESTATION OF ANIMALS

[76] Inventor: Chalmer V. Rehmert, Jr., 14419 Briarmall, San Antonio, Tex. 78247

[21] Appl. No.: 293,365

[22] Filed: Jan. 4, 1989

[51] Int. Cl.$^4$ .................... A61K 31/445; A61K 35/58
[52] U.S. Cl. ........................................ 514/315; 424/98
[58] Field of Search ........................... 424/98; 514/315

[56] References Cited

U.S. PATENT DOCUMENTS 4,822,608 4/1989 Benton et al. ........................ 424/98

OTHER PUBLICATIONS

Chem. Abst. 106: 33359j; 1987.
Chem. Abst. 105: 227099z, 1986.
Chem. Abst. 98: 54258g, 1883.
Chem. Abst. 93: 168451s, 1980.

Primary Examiner—John W. Rollins
Attorney, Agent, or Firm—Thomas E. Sisson

[57] ABSTRACT

A method for treating parasitic infestation of animals by the oral administration of a piperidine alkaloid composition over a period of days. Administration of 100–400 units of whole body extract of the imported red fire ant, Solenopsis invicta, over a period of one to eleven days with regular booster dosages disseminates the alkaloid composition through the blood and tissue fluids of the treated animals resulting in the elimination of ticks and fleas.

9 Claims, No Drawings

METHOD OF TREATING PARASITIC INFESTATION OF ANIMALS

BACKGROUND OF THE INVENTION

This invention relates to a method for treating animals with internal and external parasite infestation.

There are numerous flea, tick, and mite control products which involve external or topical treatment procedures including sprays, powders, dips and collars. Most of the existing products or procedures have proven largely ineffective with cats because of the cat's tendency to lick the product from its coat. Further, such topical products, which include pyrethrins and organophosphate insecticides under the brand names of Carbaryl, Malathion, Diazinon, and Dursban, have become increasingly less effective because the parasites have developed greater resistance to these products.

The applicant is aware of two products currently utilized for systemic treatment of ticks and fleas in dogs. These products are organophosphate insecticides under the brand names of Pro-Spot (13.8% fenthion), and Proban (cythioate) marketed by Haver, Mobay Corporation, Animal Health Division, Shawnee, Kans. 66201. Neither of these products are recommended for cats because of their toxicity. Organophospaate insecticides have been in use for some time for tick and flea control, but again, the parasites appear to be developing resistance to organophosphates and their efficacy has dropped off considerably.

The present invention offers an alternative to the known systemic parasite control products. Tests have shown the instant invention to be nearly 100% effective in eliminating flea and tick infestation. There have been no toxic effects on either dogs or cats tested. Hemograms and blood chemistries have remained normal in both dogs and cats.

SUMMARY OF THE INVENTION

The present invention is a method of treating parasitic infestation in animals by the oral administration of a sufficient amount of a piperidine alkaloid composition to effectively control the parasitic infestation. Administration of whole body extract of the imported red fire ant, Solenopsis invicta, over a period of days results in the elimination of ticks and fleas in both dogs and cats, without any toxic effects on the animals. This is particularly important in the systemic treatment of cats because of the toxicity of organophosphates to cats.

DETAILED DESCRIPTION OF THE PREFERRED EMBODIMENT

Considerable research has been done on the imported red fire ant, Solenopsis invicta. Chemical studies on the venom of this insect have shown that the venom is 95% alkaloids and the remaining 5% contains solubilized proteins and amino acids. The alkaloid fractions are characterized by the presence of various 2, 6 di-substituted piperidines. The venom also contains enzymes including hyaluronidase and phospholipase.

Of the piperidine alkaloids, Solenopsin A and Solenopsin B are the two major component with Solenopsin A being the primary component. Solenopsin A is a trans-2-methyl 6-n-undecylpiperidine. Solenopsin B is 2, 6-trans-dialkyl-piperidine. Solenopsin A and Solenopsin B may be produced synthetically.

In the present invention, live fire ants are captured and quickly frozen to preserve their freshness. Each ant contains approximately 40 nanoliters of venom. For the further purposes of this disclosure, each ant is considered to comprise approximately one unit of venom or 40 nanoliters of venom containing the alkaloids Solenopsin A and Solenopsin B.

After freezing, the ants are ground to a fine texture, inserted into soluble capsules as whole body extract, and kept frozen until administred to the animals, as will be discussed further.

While pure venom may be utilized in the treatment of parasite infestation it is more practical from a commercial standpoint to use whole body extract. Further, while synthetically produced Solenopsin A or Solenopsin B may be effective in parasite control, again, it is currently more practical commercially to use whole body extract.

It is anticipated that the freshness of the alkaloid composition may be achieved through the use of appropriately coated capsules.

In treatment for parasitic infestation of dogs weighing 4 to 80 pounds, 100 to 400 units of whole body extract of Solenopsis invicta, containing the piperidine alkaloid composition including Solenopsin A and Solenopsin B, was orally administered over a period of 11 days. The first administration of 100 to 400 units occurred on day 1, day 2 was skipped to allow the animal to react to the dosage, and for nine consecutive days the animal was orally administered 100 to 400 units daily. Complete elimination of tick and flea infestation was achieved.

Likewise, in the treatment for parasitic infestation of cats weighing 6 to 8 pounds, daily administration of 100–200 units of whole body extract of Solenopsis invicta over a period of 11 days resulted in complete elimination of flea infestation. It is anticipated that the upper end limits of dosage for cats may exceed 400 units daily. To ensure that the treated animal is not re-infested, additional dosages in the range of 100–300 units are administered once monthly thereafter; i.e., a booster dose once monthly.

It is believed that when the piperidine alkaloid composition of the whole body extract of the imported red fire ant, Solenopsis invicta, containing Solenopsin A and Solenopsin B, is ingested by dogs and cats and other small animals, the piperidine alkaloid composition dissiminates through the blood and tissue fluids of the animal. When a flea, tick, mite, or other parasite obtains a blood or tissue fluid meal from the treated animal, the parasite's body structure and functions are destroyed within a few days by the Solenopsin A or Solenopsin B, resulting in death to the parasite. Since most parasites die before they have time to reproduce, infestation is rapidly eliminated.

While the invention has been described in connection with a preferred embodiment, it is not intended to limit the invention to the particular form set forth, but, on the contrary, it is intended to cover alternatives, modifications, and equivalents, as may be included within the spirit and scope of the invention as defined by the appended claims.

I claim:

1. A method for treating blood or tissue fluid feeding parasite infestation of animals comprising the oral administration of a sufficient amount of a piperidine alkaloid composition selected from the group consisting of solenopsin A and Solenopsin B, syntheic derivatives thereof, and mixturews thereof to effectively control said infestation.

2. The method of claim 1 wherein said piperidine alkaloid composition is derived from whole body extract of *Solenopsis invicta*.

3. The method of claim 1 wherein said piperidine alkaloid composition is derived from pure venom of *Solenopsis invicta*.

4. The method of claim 1 wherein said piperidine alkaloid composition is substantially Solenopsin A and Solenpsin B.

5. The method of claim 3 wherein said sufficient amount is in the range of 100 to 400 units orally administered daily for a period of one or more days.

6. A composition for the treatment of blood or tissue fluid feeding parasite infestation of animals comprising a sufficient amount of a piperidine alkaloid selected from the group consisting of Solenopsin A and Solenopsin B, synthetic derivatives thereof, and mixtures thereof in oral and dosage unit form to effectively control said infestation when said composition is orally administered to said animal.

7. The composition of claim 6 wherein said piperidine alkaloid composition is derived from whole body extract of *Solenopsis invicta*.

8. The composition of claim 6 wherein said piperidine alkaloid composition is derived from pure venom of *Solenopsis invicta*.

9. The composition of claim 6 wherein said sufficient amount is in the range of 100 to 300 units orally administered daily for a period of one or more days.

* * * * *